US005273674A

United States Patent [19]

Kottwitz et al.

[11] Patent Number: 5,273,674

[45] Date of Patent: Dec. 28, 1993

[54] 2,5-DIACYLOXY-2,5-DIHYDROFURAN ACTIVATORS FOR INORGANIC PER COMPOUNDS

[75] Inventors: Beatrix Kottwitz; Thomas Merz, both of Duesseldorf; Rudolf Lehmann, Leichlingen, all of Fed. Rep. of Germany

[73] Assignee: Henkel Kommanditgesellschaft auf Aktien, Duesseldorf, Fed. Rep. of Germany

[21] Appl. No.: 952,908

[22] PCT Filed: May 8, 1991

[86] PCT No.: PCT/EP91/00864

§ 371 Date: Nov. 17, 1992

§ 102(e) Date: Nov. 17, 1992

[87] PCT Pub. No.: WO91/18082

PCT Pub. Date: Nov. 28, 1991

[30] Foreign Application Priority Data

May 17, 1990 [DE] Fed. Rep. of Germany ....... 4015859

[51] Int. Cl.$^5$ ..................... A61K 31/19; C11D 3/395; C11D 7/54; D06L 3/02

[52] U.S. Cl. .......................................... 252/95; 8/111; 252/89.1; 252/96; 252/97; 252/99; 252/104; 252/139; 252/173; 252/174.12; 252/186.38; 252/DIG. 14; 422/29

[58] Field of Search ..................... 8/111; 252/89.1, 95, 252/96, 97, 99, 104, 139, 173, 174.12, DIG. 14, 186.25, 186.26, 186.38; 422/29

[56] References Cited

U.S. PATENT DOCUMENTS

| | | | |
|---|---|---|---|
| 4,107,065 | 11/1984 | Gray | 252/99 |
| 4,483,778 | 11/1984 | Thompson | 252/94 |
| 4,536,314 | 8/1985 | Hardy | 252/102 |

*Primary Examiner*—Dennis Albrecht

*Attorney, Agent, or Firm*—Ernest G. Szoke; Wayne C. Jaeschke; Real J. Grandmaison

[57] ABSTRACT

2,5-diacyloxy-2,5-dihydrofurans corresponding to formula (I)

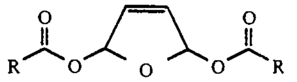

(I)

wherein R is a $C_1$–$C_8$ alkyl radical or a phenyl radical are useful as activators for inorganic per compounds in oxidizing, cleaning or disinfecting solutions.

14 Claims, No Drawings

2,5-DIACYLOXY-2,5-DIHYDROFURAN ACTIVATORS FOR INORGANIC PER COMPOUNDS

BACKGROUND OF THE INVENTION

1. Field of the Invention

This invention relates to the use of 2,5-diacyloxy-2,5-dihydrofurans as activators for inorganic peroxides and to detergents, cleaning preparations and disinfectants containing these activators.

2. Discussion of Related Art

Inorganic per compounds, more particularly hydrogen peroxide and solid per compounds which dissolve in water with evolution of hydrogen peroxide, such as sodium perborate and sodium carbonate perhydrate, have long been used as oxidizing agents for disinfection and bleaching purposes. The oxidizing effect of these substances in dilute solutions depends to a large extent on temperature. Thus, with $H_2O_2$ or perborate, for example, sufficiently rapid bleaching of soiled textiles in alkaline bleaching liquors is only achieved at temperatures above approximately 80° C. At lower temperatures, the oxidizing effect of the inorganic per compounds can be improved by addition of so-called activators, for which numerous proposals have been made in the literature, above all from the classes of N- or O-acyl compounds, for example polyacylated alkylenediamines, more particularly tetraacetyl ethylenediamine, acylated glycol urils, more particularly tetraacetyl glycol uril, N-acylated hydantoins, hydrazides, triazoles, urazoles, diketopiperazines, sulfuryl amides and cyanurates, also carboxylic anhydrides, more particularly phthalic anhydride, carboxylic acid esters, more particularly sodium isononanoyl phenyl sulfonate and acylated sugar derivatives, such as pentaacetyl glucose. The bleaching effect of water-based peroxide liquors can be increased by addition of these substances to such an extent that substantially the same effects are obtained at temperatures as low as 60° C. as are obtained with the peroxide liquor alone at 95° C.

In the efforts being made to develop energy-saving washing and bleaching processes, application temperatures well below 60° C. and, more particularly, below 45° C. down to the temperature of cold water have acquired increasing significance in recent years.

Unfortunately, the effect of hitherto known activators clearly diminishes at these low temperatures. Accordingly, there has been no shortage of attempts to develop more effective activators for this temperature range although there has not yet been any evidence of real success. The problem addressed by the present invention also was to improve the oxidizing and bleaching effect of inorganic per compounds at low temperatures below 80° C. and, more particularly, in the range from about 15° C. to 45° C.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that a remarkable increase in the oxidizing and bleaching effect of inorganic per compounds in oxidation, bleaching and wash liquors is achieved in this temperature range by the use of certain 2,5-diacyl-oxy-2,5-dihydrofurans as activators. The activators in question are substances selected from compounds corresponding to formula (I)

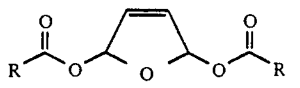

(I)

in which R is a $C_{1-8}$ alkyl radical or the phenyl radical, and mixtures thereof. Compounds corresponding to formula (I), in which $R=C_{1-4}$ alkyl, and mixtures thereof are particularly preferred. The present invention also relates to detergents, cleaning preparations and disinfectants containing such activators and to a process for activating inorganic per compounds.

The 2,5-diacyloxy-2,5-dihydrofurans corresponding to formula (I) to be used in accordance with the invention may be produced by chemical or electrochemical oxidation of furan by processes known in principle, for example as described in DE-OS 26 01 543, in GB-PSS 642,277 and 703,297, by N. Elming and N. Clauson-Kaas in Acta Chem. Scand. 6 (1952), 535 or by A.J. Baggaley and R. Brettle in J. Chem. Soc. (C) 1968, 969.

In the process according to the invention, the compounds in question may be used as activators in any applications where it is important to obtain a particular increase in the oxidation effect of inorganic per compounds at low temperatures, for example in the bleaching of textiles, hair or hard surfaces, in the oxidation of organic or inorganic intermediate products and in disinfection.

The use according to the invention comprises establishing conditions under which hydrogen peroxide and 2,5-diacyloxy-2,5-dihydro can react with one another with the object of obtaining products which have a stronger oxidizing effect. Such conditions prevail in particular when both reactants are contacted with one another in aqueous solution. This can be done by separate addition of the per compound and the activator to a solution optionally containing detergents or cleaning preparations. However, the process according to the invention is carried out with particular advantage using a detergent, cleaning preparation or disinfectant according to the invention containing the activator and, optionally, a peroxidic oxidizing agent. The per compound may also be added to the solution separately, in bulk or in the form of a preferably aqueous solution or suspension where a peroxide-free preparation is used.

The conditions may be varied within wide limits according to the application envisaged. Thus, in addition to purely aqueous solutions, mixtures of water and suitable organic solvents may also be used as the reaction medium. The quantities of per compounds used are generally selected so that the solution contains between 10 ppm and 10% active oxygen and preferably between 50 and 5000 ppm active oxygen. The quantity of activator used also depends on the application envisaged. The activator is used in a quantity of 0.03 to 1 mol and preferably in a quantity of 0.1 to 0.5 mol per mol inorganic per compound, depending on the desired degree of activation. In special cases, however, it may also be used in larger or smaller quantities.

A detergent, cleaning preparation or disinfectant according to the invention preferably contains 0.2% by weight to 30% by weight and, more particularly, 1% by weight to 20% by weight of the activator according to the invention. The activator used may be adsorbed to supports and/or encapsulated in shell-forming substances. as known in principle.

The detergents, cleaning preparations and disinfectants according to the invention, which may be present in the form of powder-form solids, homogeneous solutions or suspensions, may in principle contain any known ingredients typical of such preparations in addition to the activator according to the invention in the form of a compound corresponding to formula (I) or mixtures of such compounds. More particularly, the detergents and cleaning preparations according to the invention may contain builders, surfactants, inorganic per compounds, water-miscible organic solvents, enzymes, sequestrants, electrolytes, pH regulators and other auxiliaries, such as optical brighteners, redeposition inhibitors, foam regulators, additional peroxide activators, dyes and fragrances.

In addition, a cleaning preparation according to the invention for hard surfaces may contain abrasive constituents, more particularly from the group consisting of silica flours, sawdusts, powdered plastics, chalks and glass microbeads or mixtures thereof. The cleaning preparations according to the invention preferably contain no more than 20% by weight and, more particularly, between 1% by weight and 10% by weight abrasives.

To enhance its disinfecting effect on special germs, a disinfectant according to the invention may contain typical antimicrobial agents in addition to the ingredients mentioned above. The disinfectants according to the invention preferably contain no more than 10% by weight and, more particularly, between 0.1 and 5% by weight of such antimicrobial additives.

The preparations according to the invention contain one or more surfactants, more particularly anionic surfactants, nonionic surfactants and mixtures thereof. Suitable nonionic surfactants are, in particular, alkyl glycosides and ethoxylation and/or propoxylation products of alkyl glycosides or linear or branched alcohols containing 12 to 18 carbon atoms in the alkyl component and 3 to 20 and preferably 4 to 10 alkyl ether groups. It is also possible to use corresponding ethoxylation and/or propoxylation products of N-alkylamines, vicinal diols and fatty acid amides, which correspond to the long-chain alcohol derivatives mentioned in regard to the alkyl component, and alkylphenols containing 5 to 12 carbon atoms in the alkyl radical.

Suitable anionic surfactants are, in particular, soaps and those containing sulfate or sulfonate groups with, preferably, alkali metal ions as cations. Preferred soaps are the alkali metal salts of saturated or unsaturated $C_{12-18}$ fatty acids. Fatty acids such as these may also be used in incompletely neutralized form. Suitable surfactants of the sulfate type include the salts of sulfuric acid semiesters of $C_{12-18}$ fatty alcohols and the sulfation products of the nonionic surfactants mentioned with low degrees of ethoxylation. Suitable surfactants of the sulfonate type include linear alkylbenzene sulfonates containing 9 to 14 carbon atoms in the alkyl component, alkane sulfonates containing 12 to 18 carbon atoms and olefin sulfonates containing 12 to 18 carbon atoms, which are formed in the reaction of corresponding monoolefins with sulfur trioxide, and also α-sulfofatty acid esters which are formed in the sulfonation of fatty acid methyl or ethyl esters.

These surfactants are present in the cleaning preparations or detergents according to the invention in quantities of, preferably, 5% by weight to 50% by weight and, more preferably, 8% by weight to 30% by weight while the disinfectants according to the invention preferably contain 0.1% by weight to 20% by weight and, more preferably, 0.2% by weight to 5% by weight surfactants.

Suitable per compounds are, in particular, hydrogen peroxide and inorganic salts which release hydrogen peroxide under the cleaning conditions, such as perborate, percarbonate and/or persilicate. If solid per compounds are to be used, they may be used in the form of powders or granules which may also be encapsulated in known manner. The per compounds may be added to the cleaning liquor as such or in the form of preparations containing the per compounds and, in principle, any typical constituents of detergents, cleaning preparations or disinfectants. Hydrogen peroxide is preferably used in the form of aqueous solutions containing 3 to 10% by weight hydrogen peroxide. If a detergent or cleaning preparation according to the invention contains per compounds, they are present in quantities of preferably not more than 50% by weight and, more preferably, between 5 and 30% by weight while disinfectants according to the invention preferably contain per compounds in quantities of 0.5% by weight to 40% by weight and, more preferably, in quantities of 5% by weight to 20% by weight.

Suitable builders, which may be used individually or in admixture, are those from the classes of polycarboxylic acids, more particularly polymers of acrylic acid, methacrylic acid and maleic acid and copolymers thereof, aminopolycarboxylic acids, more particularly nitrilotriacetic acid and ethylenediamine tetraacetic acid, polyphosphonic acids, more particularly aminotri(methylenephosphonic acid), ethylenediamine tetra(methylenephosphonic acid) and 1-hydroxyethane-1,1-diphosphonic acid, polyphosphates, more particularly sodium triphosphate, layer silicates, more particularly bentonites, and aluminosilicates, more particularly zeolites, preferably zeolites of the NaA or NaX type. The acids mentioned above are typically used in the form of their alkali metal salts, more particularly their sodium or potassium salts. The builders are present in the detergents or cleaning preparations according to the invention in quantities of preferably not more than 60% by weight and, more preferably, in quantities of 5% by weight to 40% by weight while the disinfectants according to the invention are preferably free from builders which merely complex the components responsible for water hardness and preferably contain not more than 20% by weight and, more particularly, between 0.1% by weight and 5% by weight heavy metal complexing agents, preferably from the group consisting of aminopolycarboxylic acids, aminopolyphosphonic acids and hydroxypolyphosphonic acids and their water-soluble salts and also mixtures thereof.

Suitable enzymes are those from the class of proteases, lipases and amylases and also mixtures thereof. Enzymatic agents obtained from fungi or bacterial strains, such as Bacillus subtilis, Bacillus licheniformis and Streptomyces griseus, are particularly suitable. The enzymes used may be adsorbed to supports and/or encapsulated in shell-forming substances to protect them against premature inactivation. They are preferably present in the detergents, cleaning preparations and disinfectants according to the invention in quantities of not more than 1% by weight and, more preferably, in quantities of 0.2% by weight to 0.7% by weight.

Organic solvents which may be used in the preparations according to the invention, particularly where they are present in liquid form, include $C_{1-4}$ alcohols, more particularly methanol, ethanol, isopropanol and tert. butanol, $C_{2-4}$ diols, more particularly ethylene glycol and propylene glycol, and mixtures thereof. Water-miscible solvents such as these are present in the detergents, cleaning preparations and disinfectants according to the invention in quantities of preferably not more than 30% by weight and, more preferably, in quantities of 6% by weight to 20% by weight.

To establish a desired pH value, which is not spontaneously adjusted by the mixture of the remaining components, the preparations according to the invention may contain system-compatible and ecologically safe acids, more particularly citric acid, acetic acid, tartaric acid, malic acid, lactic acid, glycolic acid, succinic acid, glutaric acid and/or adipic acid, and also mineral acids, more particularly sulfuric acid, or bases, more particularly ammonium or alkali metal hydroxides. These pH regulators are present in the preparations according to the invention in quantities of preferably not more than 20% by weight and, more preferably, in quantities of 1.2% by weight to 17% by weight.

The production of the solid preparations according to the invention does not involve any difficulties and may be carried out by methods known in principle, for example by spray drying or granulation, the per compound and activator optionally being separately added at a later stage. Detergents, cleaning preparations or disinfectants in the form of aqueous solutions or solutions containing other typical solvents are produced with particular advantage by simple mixing of the ingredients which may be introduced into an automatic mixer either in bulk or in solution.

EXAMPLES

Example 1: Preparation of the activators 1. 2,5-diacetoxy-2,5-dihydrofuran 97.5 g lead (IV) acetate were added in portions with stirring at 50° C. to a mixture of 180 ml glacial acetic acid and 115 ml acetanhydride. After addition of 14.9 g furan, the reaction mixture was heated for 1.5 hours to 60 to 65° C. The solvent was then largely removed in vacuo (approx. 10 torr, bath temperature 60° C.). 400 ml anhydrous diethyl ether were added to the residue which was then subjected to fractional distillation after filtration and removal of the solvent. 24.5 g 2,5-diacetoxy-2,5-dihydrofuran were obtained in the boiling range from 81° C. to 85° C./0.01 torr in the form of a gas chromatographically 99% pure liquid having a refractive index $n_D^{25}$ of 1.4538.

2. 2,5-dipropionyloxy-2,5-dihydrofuran

A mixture of 130 ml propionic acid, 51.3 g lead (IV) propionate (prepared by the method described by D.H. Hey, C.J.M. Stirling and G.H. Williams in J. Chem. Soc. 1954, 2747) and 7.0 g furan was heated for 35 minutes to 55°-60° C. and for 45 minutes to 60°-65° C. Subsequent fractional distillation gave 12.0 g 2,5-dipropionyloxy-2,5-dihydrofuran in the boiling range from 110° C. to 116° C. /0.5 torr in the form of a gas chromatographically 98% pure liquid having a refractive index $n_D^{25}$ of 1.4525.

3. 2,5-dibutyroxy-2,5-dihydrofuran

Following the procedure described in 2, 2,5-dibutyroxy-2,5-dihydrofuran is obtained from 36.5 g lead (IV) butyrate, 135 ml butyric acid and 4.5 g furan in the boiling range from 104° C. to 108° C./0.2 torr in the form of a gas chromatographically 98% pure liquid having a refractive index $n_D^{25}$ of 1.4496.

4. 2,5-dibenzoyloxy-2,5-dihydrofuran

A mixture of 100 g benzoic acid, 67.5 g lead (IV) benzoate (produced by the method described in J. Chem. Soc. 1954, 2747) and 10.2 g furan was heated for 1 hour to 50° C. and for 3 hours to 75° C. After cooling to room temperature, filtration and removal of excess furan in vacuo, 26 g 2,5-dibenzoyloxy-2,5-dihydrofuran melting at 190 to 196° C. crystallized out from the residue after addition of 100 ml dioxane and cooling to approx. 0° C.

5. 2,5-dipentanoyloxy-2,5-dihydrofuran

Following the procedure described in 4, 17.3 g 2,5-dipentanoyloxy-2,5-dihydrofuran melting at 30 to 35° C. were obtained from 68.2 g lead (IV) valerate, 100 ml valeric acid and 7.6 g furan.

Example 2

Liquid detergents D1 and D2 and liquid detergents D3 and D4 additionally containing 2,5-diacetoxy-2,5-dihydrofuran were produced simply by mixing their constituents in the quantities shown in Table 1. Instead of the bleach activator 2,5-diacetoxy-2,5-dihydrofuran, 2,5-dibutyroxy-2,5-dihydrofuran (D5), 2,5-dipentanoyloxy-2,5(D6) or 2,5-dibenzoyloxy-2,5-dihydrofuran (D7) was incorporated in formulations which otherwise corresponded to detergent D4.

TABLE 1

| | Detergent composition [% by weight] | | | |
|---|---|---|---|---|
| | D1 | D2 | D3 | D4 |
| Na—$C_{10-13}$alkylbenzene sulfonate | 12 | 12 | 12 | 12 |
| Ethoxylated $C_{13-15}$ fatty alcohol (7 EO) | 15 | 15 | 15 | 15 |
| $C_{16-18}$ fatty acid | 5 | 5 | 5 | 5 |
| $C_{12-14}$ fatty acid | 10 | 10 | 10 | 10 |
| Diethylene triamine pentamethylene phosphonic acid sodium salt | 1 | 1 | 1 | 1 |
| Monoethanolamine | 5 | 0 | 5 | 0 |
| Ethanol | 7 | 7 | 7 | 7 |
| Sodium hydroxide | 3 | 3 | 3 | 3 |
| Citric acid | 0.5 | 0.5 | 0.5 | 0.5 |
| Enzyme (protease) | 0.5 | 0.5 | 0.5 | 0 |
| Optical brightener (Blankophor ® MBBH) | 0.2 | 0.2 | 0.2 | 0.2 |
| 2,5-diacetoxy-2,5-dihydrofuran | 0 | 0 | 2 | 2 |
| Water | ad 100 | | | |

Aqueous solutions containing quantities of 0.9 g of the detergents mentioned and 2 ml red wine per 100 ml were examined by UV/Vis spectroscopy (measuring wavelength 460 nm). The reductions in the dye concentration (δc) shown in Table 2 were observed after a reaction time of 30 minutes at 30° C. In a launderometer of the Atlas Standard Type (250 ml liquor volume, water hardness 17° Gh), quantities of 2.1 g fabrics soiled with the test soils indicated in Table 3 were washed for 30 minutes (including heating time (3° C./minute)) with quantities of 6.3 g clean ballast fabrics of white cotton at 40° C or 60° C. with detergent D2 (9.25 grams per liter washing solution) and then rinsed three times for 30 seconds (column I). After drying, the remission of the apparently clean test fabrics, based on $BaSO_4$-100%, was photometrically determined (measuring wavelength 460 nm). For comparison, the same washing solution, to which 2% by weight hydrogen peroxide —expressed as 100% substance - had been added (column II) and a washing solution containing 9.25 g per liter of detergent D4 and 2% by weight hydrogen peroxide (column III) were tested under the same conditions.

TABLE 2

| Reduction in dye concentration | |
|---|---|
| Detergent | δc[%] |
| D1 | 0 |
| D1 + 2% by weight $H_2O_2$ | 9 |
| D3 + 2% by weight $H_2O_2$ | 52 |

TABLE 3

| | Remission values [%] | | | | | |
|---|---|---|---|---|---|---|
| | I | | II | | III | |
| Soil | [40° C.] | [60° C.] | [40° C.] | [60° C.] | [40° C.] | [60° C.] |
| A | 56.1 | 60.2 | 56.4 | 60.3 | 60.2 | 63.3 |
| B | 60.5 | 65.2 | 61.5 | 67.8 | 64.9 | 70.0 |
| C | 61.8 | 64.7 | 62.6 | 65.7 | 64.1 | 67.3 |
| D | 46.5 | 47.0 | 48.0 | 50.4 | 51.5 | 54.0 |
| E | 55.0 | 49.0 | 55.2 | 51.7 | 57.2 | 59.8 |
| F | 52.8 | 54.1 | 53.7 | 57.0 | 56.6 | 58.3 |
| G | 57.3 | 56.9 | 59.1 | 59.8 | 62.8 | 64.5 |

Soils: A = red wine on cotton; B = tea on cotton; C = coffee on cotton; D = red wine on crease-resistant cotton; E = tea on crease-resistant cotton; F = red wine on cotton/polyester blend; G = tea on cotton/polyester blend.

The remission values tabulated in Table 3 demonstrate the superior bleaching effect of the formulation containing the activator according to the invention by comparison with the activator-free and peroxide-free detergent (column I) and with the activator-free, but peroxide-containing detergent (column II).

Example 3: Testing of stability in storage

After storage for 14 days at room temperature, the content of bleach activator in the liquid detergents according to the invention listed in the following Table was determined by the test based on the decoloring of Brilliant Green. To this end, 100 μl of a 0.1% by weight solution (water/ethanol 1:1) of Brilliant Green (Aldrich) were added similarly to the method described in Example 2 to quantities of 100 ml of an aqueous solution containing 0.9 g of a detergent according to Table 4 and 2 % by weight $H_2O_2$. The content of bleach activator in the particular detergent was determined by UV/Vis-spectroscopic measurement of the reduction in the dye concentration.

TABLE 4

| Detergent | Content of bleach activator [% by weight] |
|---|---|
| D4 | 1.96 |
| D5 | 1.96 |
| D6 | 1.98 |
| D7 | 1.99 |

We claim:

1. The process of activating an inorganic per compound in an oxidizing, cleaning or disinfecting solution, comprising adding to said solution a 2,5-diacyloxy-2,5-dihydrofuran activator compound corresponding to formula (I)

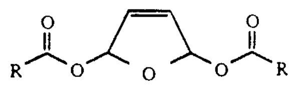

(I)

wherein R is a $C_1$14 $C_8$ alkyl radical or a phenyl radical, said activator compound being added in an amount effective to activate said inorganic per compound, and wherein said inorganic per compound is added to said solution prior to, simultaneously, or subsequent to addition of said activator compound.

2. A process as in claim 1 wherein said solution comprises an aqueous surfactant-containing solution.

3. A process as in claim 1 wherein said per compound comprises a peroxide-containing bleaching agent.

4. A process as in claim 1 wherein in said compound corresponding to formula (I), R is a $C_1$–$C_4$ alkyl radical.

5. A process as in claim 1 wherein said per compound is selected from the group consisting of hydrogen peroxide, perborate, percarbonate, and mixtures thereof.

6. A surfactant-containing composition useful for oxidizing, cleaning or disinfecting an article, said composition containing a 2,5-diacyloxy 2,5-dihydrofuran activator compound corresponding to formula (I)

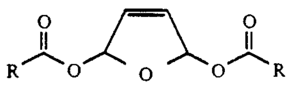

(I)

wherein R is a $C_1$14 $C_8$ alkyl radical or a phenyl radical, said activator compound being present in an amount effective to activate an inorganic per compound.

7. A composition as in claim 6 wherein in said compound corresponding to formula (I), R is a $C_1$–$C_4$ alkyl radical.

8. A composition as in claim 6 further containing from an oxidizing effective amount up to about 50% by weight of a per compound selected from the group consisting of hydrogen peroxide, perborate, percarbonate and mixtures thereof, based on the weight of said compound.

9. A composition as in claim 6 containing from about 0.2 to about 30% by weight of said activator compound, from about 0.5 to about 40% by weight of a per compound selected from the group consisting of hydrogen peroxide, perborate, percarbonate and mixtures thereof, from about 0.1 to about 20% by weight of an anionic or nonionic surfactant, from 0 to about 20% by weight of a water hardness complexing agent, from 0 to about 1% by weight of an enzyme, from 0 to about 30% by weight of an organic solvent, from 0 to about 20% by weight of a pH regulator, and from 0 to about 10% by weight of an additional antimicrobial agent.

10. A composition as in claim 6 containing from about 0.2 to about 30% by weight of said activator compound, from about 5 to about 50% by weight of an anionic or nonionic surfactant, from 0 to about 60% by weight of a builder component, from 0 to about 1% by weight of an enzyme, from 0 to about 30% of an organic solvent, and from 0 to about 20% by weight of a pH regulator, all weights being based on the weight of said composition.

11. A composition as in claim 10 containing from about 5 to about 40% by weight of a builder component selected from the group consisting of polycarboxylic acid, aminopolycaroxylic acid, polyphosphonic acid, polyphosphate, layer silicate and aluminosilicate; from about 0.2 to about 0.7% by weight of an enzyme; from about 6 to about 20% by weight of an organic solvent selected from the group consisting of a $C_1$-$C_4$ alcohol, $C_2$-$C_4$ diol and mixtures thereof; and from about 1.2 to about 17% by weight of a pH regulator, all weights being based on the weight of said composition.

12. A composition as in claim 10 further containing up to about 20% by weight of an abrasive selected from the group consisting of silica flour, sawdust, powdered plastic, chalk, glass microbeads, and mixtures thereof, based on the weight of said composition.

13. A composition as in claim 11 further containing up to about 20% by weight of an abrasive selected from the group consisting of silica flour, sawdust, powdered plastic, chalk, glass microbeads and mixtures thereof, based on the weight of said composition.

14. A composition as in claim 18 further containing from an oxidizing effective amount up to about 50% by weight of a per compounds selected from the group consisting of hydrogen peroxide, perborate, percarbonate and mixtures thereof, based on the weight of said composition.

* * * * *